United States Patent
Maiden

(10) Patent No.: US 8,917,393 B2
(45) Date of Patent: Dec. 23, 2014

(54) METHOD AND APPARATUS FOR PROVIDING IMAGE DATA

(75) Inventor: Andrew Maiden, Penrith (GB)

(73) Assignee: Phase Focus Limited (GB)

( * ) Notice: Subject to any disclaimer, the term of this patent is extended or adjusted under 35 U.S.C. 154(b) by 317 days.

(21) Appl. No.: 12/808,661

(22) PCT Filed: Dec. 4, 2008

(86) PCT No.: PCT/GB2008/051154
§ 371 (c)(1), (2), (4) Date: Jun. 16, 2010

(87) PCT Pub. No.: WO2009/077779
PCT Pub. Date: Jun. 25, 2009

(65) Prior Publication Data
US 2011/0001970 A1 Jan. 6, 2011

(30) Foreign Application Priority Data

Dec. 17, 2007 (GB) .................................. 0724448.6

(51) Int. Cl.
G01N 21/00 (2006.01)
G01N 23/205 (2006.01)
G01N 21/47 (2006.01)
G01T 1/29 (2006.01)
G01N 21/88 (2006.01)

(52) U.S. Cl.
CPC ............ G01N 23/205 (2013.01); G01N 21/474 (2013.01); G01T 1/2914 (2013.01); G01N 21/8806 (2013.01); G01N 2223/645 (2013.01)
USPC ..................... 356/342; 356/237.1; 356/237.4; 382/210; 382/324

(58) Field of Classification Search
USPC ......................................... 356/342, 336, 335
See application file for complete search history.

(56) References Cited

U.S. PATENT DOCUMENTS

| 3,689,772 | A |   | 9/1972 | Nicholas et al. |
| 5,341,213 | A | * | 8/1994 | Giroux .......................... 356/509 |
| 5,523,846 | A | * | 6/1996 | Haga .............................. 356/445 |
| 6,630,996 | B2 |  | 10/2003 | Rao et al. |
| 2008/0095312 | A1 | * | 4/2008 | Rodenburg et al. ............. 378/87 |
| 2010/0241396 | A1 | * | 9/2010 | Rodenburg ................... 702/167 |

FOREIGN PATENT DOCUMENTS

WO WO2005/106531 A 11/2005

OTHER PUBLICATIONS

International Preliminary Report on Patentability and Written Opinion of the International Searching Authority, mailed Jul. 1, 2010, for corresponding International Application No. PCT/GB2008/051154.
International Search Report and the Written Opinion of the International Searching Authority, mailed Sep. 10, 2009, for corresponding International Application No. PCT/GB2008/051154.

* cited by examiner

*Primary Examiner* — Tarifur Chowdhury
*Assistant Examiner* — Isiaka Akanbi
(74) *Attorney, Agent, or Firm* — Wilmer Cutler Pickering Hale and Dorr LLP

(57) ABSTRACT

A method and apparatus are disclosed for providing image data for generating an image of a region of a target object. The method includes the steps of providing incident radiation, focusing the radiation downstream or upstream of a target object and via at least one detector located downstream of a focusing element, detecting an intensity of radiation scattered by the target object at an observation plane offset from a back focal plane associated with the focusing element.

28 Claims, 8 Drawing Sheets

METHOD AND APPARATUS FOR PROVIDING IMAGE DATA

CROSS REFERENCE TO RELATED APPLICATIONS

This is the U.S. National Stage of International Application No. PCT/GB2008/051154, filed Dec. 4, 2008, which in turn claims the benefit of and priority to Great Britain Application No. GB0724448.6, filed Dec. 17, 2007.

The present invention relates to a method and apparatus for providing image data suitable for generating an image of a region of a target object. In particular, but not exclusively, the present invention relates to an imaging process in which an intensity of radiation scattered by a target object is detected at an observation plane which is offset from a back focal plane of a lens (or other such focusing element) used during imaging.

Figure 1:
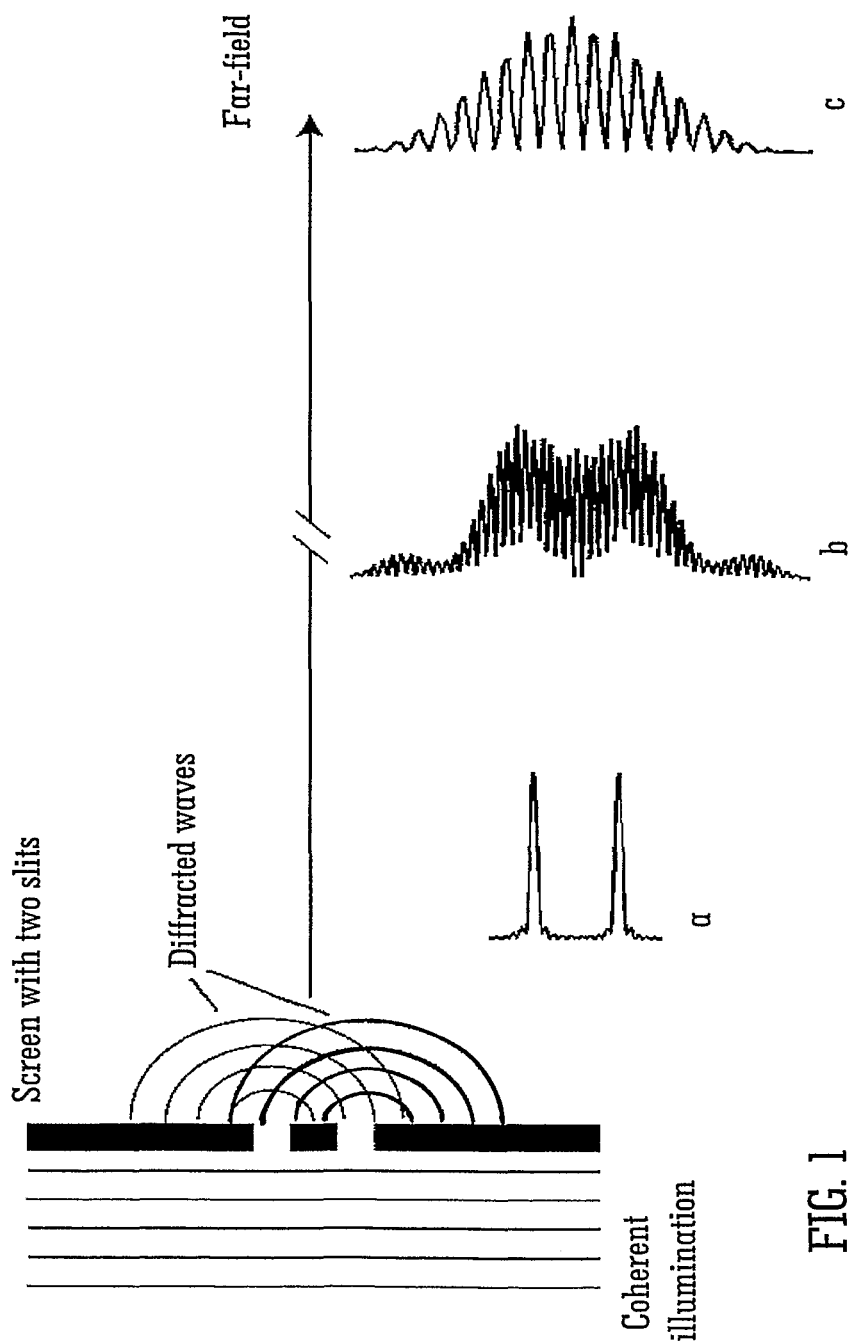

Diffraction occurs when light, or any wave phenomenon, interacts with a boundary between two different mediums. Examples could be the wave patterns formed by water around harbour walls, or the fuzzy edge of a shadow, which would be very sharply defined were it not for diffraction. A diffraction pattern is formed when a wave interacts with a structure containing many such boundaries, each of which will delay the wave and change its magnitude to different extents. The change in magnitude and phase delay of the incident wave can be expressed mathematically as the transmission function of the diffracting structure, which is a complex number $A\exp(j\phi)$. $0 \leq A \leq 1$ represents the change in magnitude, $-\pi \leq \phi \leq \pi$ represents the phase delay. Particularly well defined diffraction patterns are formed when a wave that hits such a structure is coherent (that is, when the location of the peaks and troughs in the wave are well defined). In this case, the wave can interfere constructively or destructively to form bright and dark areas. The classic 'Young's Slits' experiment illustrates this effect well and is illustrated in FIG. 1 along with expected diffraction patterns (a-c) which vary depending upon a distance away from the adjacent slits.

When the distance between a diffracting structure and the plane of observation of the diffraction pattern becomes large, the far-field condition will be met. Diffraction patterns formed in the far-field are particularly useful for two reasons. Firstly their relationship to the transmittance characteristics of the diffracting structure is accurately modelled by a Fourier Transform (a well understood and powerful mathematical function that is also easily implemented on a computer). Secondly the introduction of a focusing element between the structure and the plane of observation causes a far-field diffraction pattern to be imaged in its back focal plane. The focusing element may be a lens or a zone plate, or indeed any element which focuses an incident plane wave to a point at a well defined location.

Figure 2:
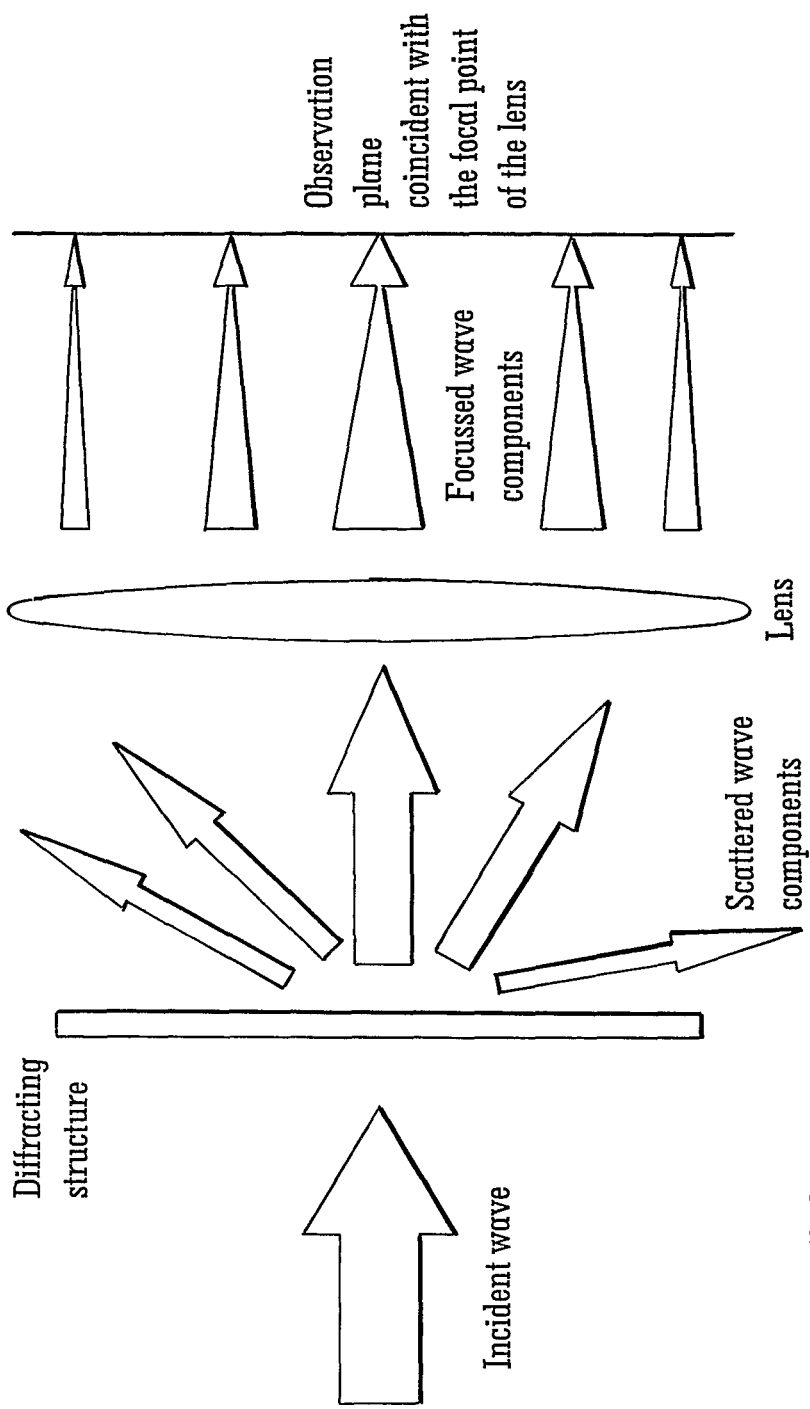

FIG. 2 illustrates imaging of a target object which scatters incident radiation and how a lens can be used as a focusing element to focus scattered wave components at an observation plane coincident with a focal point of the lens.

Provided distortions introduced by aberrations in the focusing element can be quantified, the quality of the focusing element need not be too high. This is in contrast to other conventional imaging systems where the quality of the image is highly dependent upon the quality of the lenses used; it is easier to form a diffraction pattern using an aberrated lens than it is to produce an image.

Diffraction patterns can be used to infer a great deal about the structure from which they are formed, thanks to the Fourier Transform relationship and a good understanding of the way waves behave. However where the nature of the diffracting structure is such that in the back focal plane of a lens, there is a large difference between the maximum and minimum light intensities over the area of the recording device, problems can occur in the accurate recording of the diffraction pattern. This might typically occur when the diffracting structure does not have a large effect on the incident wave.

Under these circumstances when an incident wave reaches the diffracting structure, it is scattered into a number of different waves travelling onward at a broad spread of angles. If this scattering effect is small, there will still be a large wave component travelling straight through the structure with a zero or close to zero scattering angle hence a great intensity. In comparison the more scattered waves will be significantly less intense. The effect of a lens is to cause focusing each wave component to a point on the observation plane. The location of this point is determined by the scattering angle of the particular wave component, thus those waves with a large scattering angle are focussed at points far removed from the centre of the observation plane, whilst the large wave component that traveled unaffected through the diffracting structure is focussed at a point directly in the middle. If a recording device, such as a CCD camera, is placed in the observation plane, the device will record something similar to that shown in FIG. 3. The bright spot in the centre of the figure corresponds to this unaffected 'straight through' wave, the rings and spots further out represent the waves scattered by the structure.

Unfortunately in practice, it is very difficult to record this pattern because the difference between the highest and lowest intensities in the observation plane is very large.

Recording devices can only capture a limited part of this range before they either saturate, due to the large intensities, or the signal disappears in noise when the intensity is low.

One known method of accurately recording a diffraction pattern with a high dynamic range (that is, a large difference between the highest and lowest intensity levels) is to stitch together patterns collected by the recording device at different exposure lengths. The low intensity data gathered from the high exposure patterns can then be combined with the high intensity data taken from the low exposures to produce a single pattern with a greater dynamic range, without compromise to the sensitivity of the camera. In fact often the detail at the edges of a first exposure are lost as the exposure time is reduced; it is only in the combined pattern that both the centre and extremities of the pattern are faithfully reproduced. This technique is reasonably effective, but relies on accurate knowledge of the response of the CCD and minimal movement and vibrations in the system between exposures; it may also be difficult in some circumstances to reduce the exposure time to such a degree that the centre of the pattern is not saturated. In addition, the time required to record all of this data can be unnecessarily large.

It is an aim of the present invention to at least partly mitigate the above-mentioned problems.

It is an aim of embodiments of the present invention to provide a method and apparatus for providing image data suitable for generating an image of a region of a target object.

It is an aim of embodiments of the present invention to provide a method and apparatus for detecting intensity of radiation scattered by a target object which avoids saturation of detectors located at a central region with respect to a formed diffraction pattern.

It is an aim of embodiments of the present invention to provide an iterative method for determining image data in which steps in the iterative process are incorporated to adjust for the fact that an observation plane at which intensity is detected is offset from a back focal plane associated with a focusing element.

According to a first aspect of the present invention there is provided a method of providing image data for generating an image of a region of a target object, comprising the steps of:
providing incident radiation, from a radiation source;
focusing radiation via at least one focusing element located downstream or upstream of a target object; and
via at least one detector located downstream of the focusing element, detecting an intensity of radiation scattered by the target object, at an observation plane offset from a back focal plane associated with the focusing element.

According to a second aspect of the present invention there is provided a computer program comprising program instructions for causing a computer to perform the process of any of claims 1 to 19.

According to a third aspect of the present invention there is provided apparatus for providing image data for generating an image of a region of a target object, comprising:
a radiation source that provides incident radiation;
at least one focusing element, that focuses the radiation, located downstream or upstream of a target object; and
at least one detector located downstream of the focusing element, that detects an intensity of radiation scattered by the target object at an observation plane offset from a back focal plane associated with the focusing element.

Embodiments of the present invention provide a method and apparatus for providing image data in which intensity of radiation scattered by a target object is detected by at least one detector located downstream of a focusing element used to focus radiation. The detector is located at an observation plane offset from a back focal plane associated with the focusing element. As a result the dynamic range associated with a recorded diffraction pattern is reduced. The focusing element may be a lens or zone plate or indeed any element which operates to focus an incident plane wave to a point at a predetermined location. The focusing element can be a single or multi-part device.

Embodiments of the present invention provide a modification to a Fourier transform utilised to model propagation of waves between a plane of observation, a back focal plane associated with a focusing element, such as a lens, and a plane associated with a target object.

Figure 3:
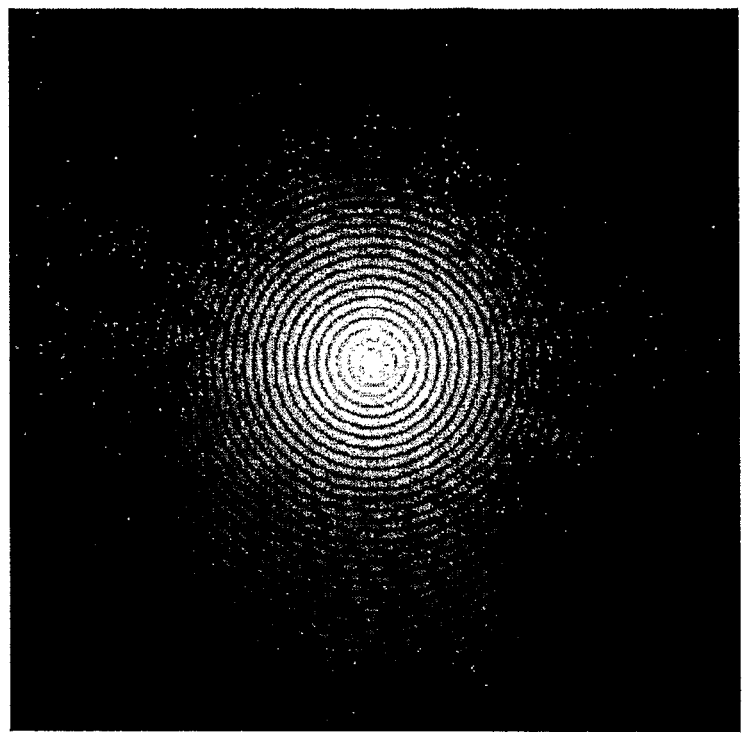
Figure 4:
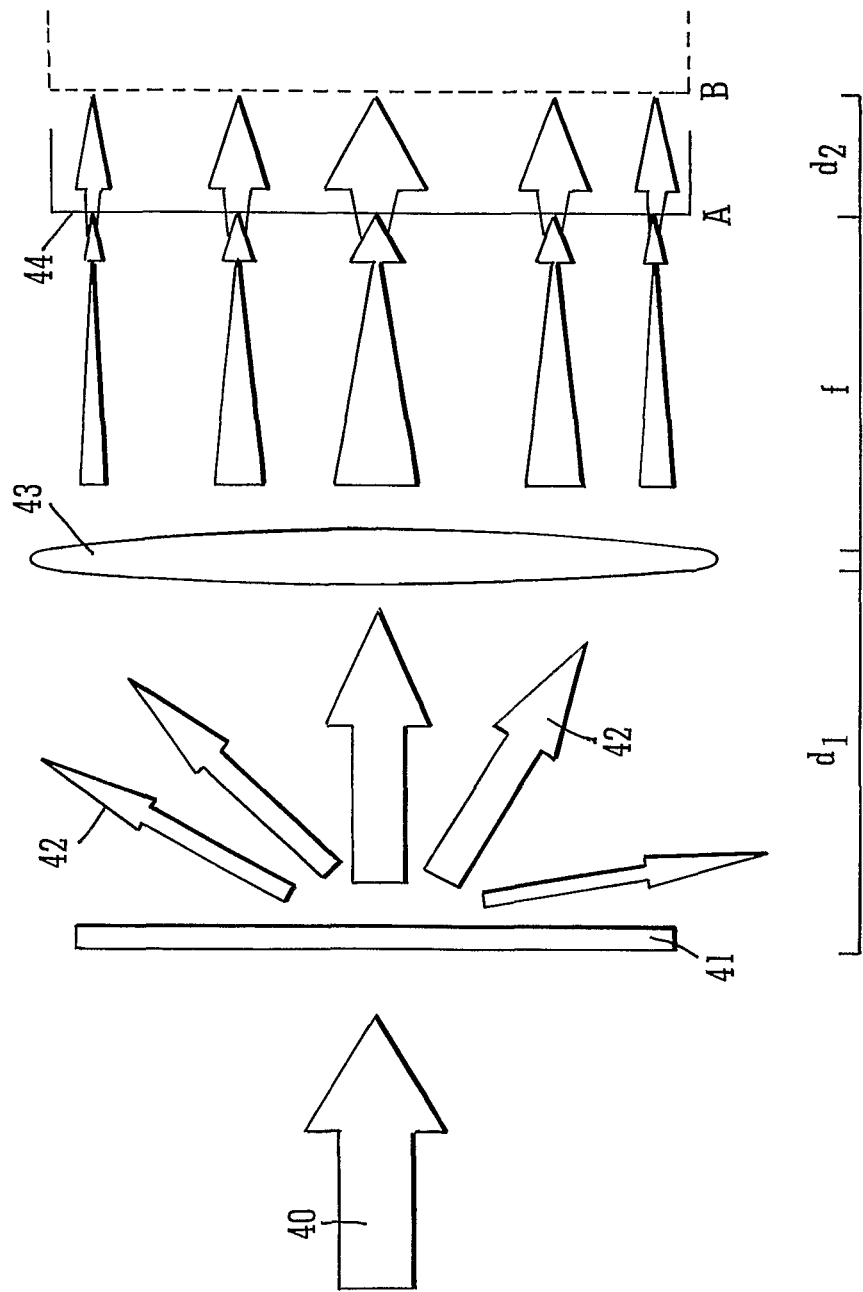
Figure 5:
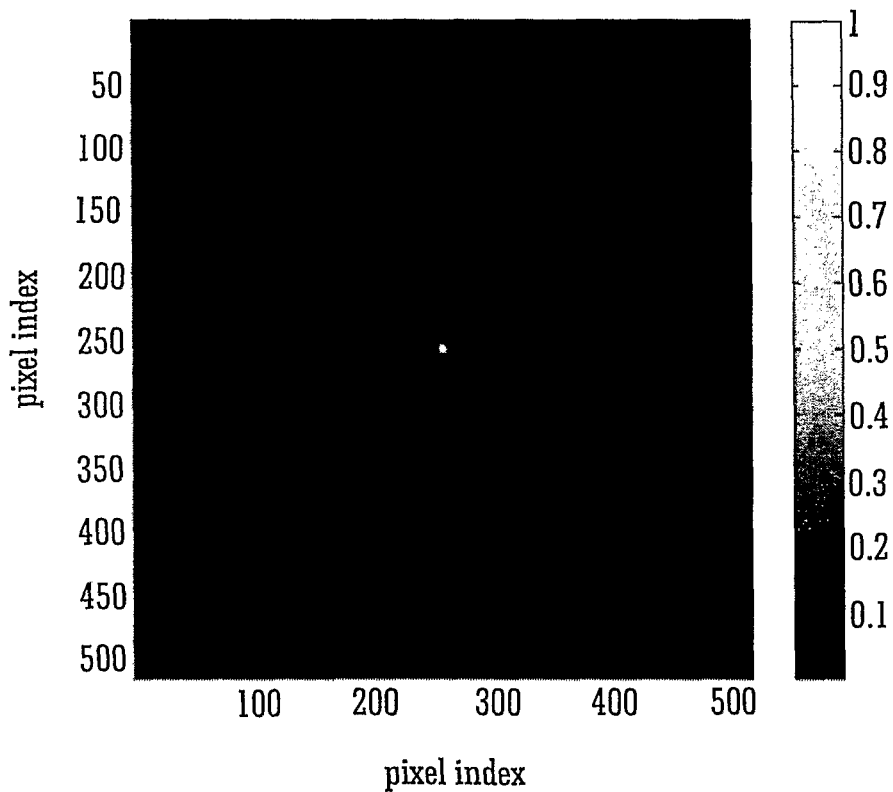
Figure 6:
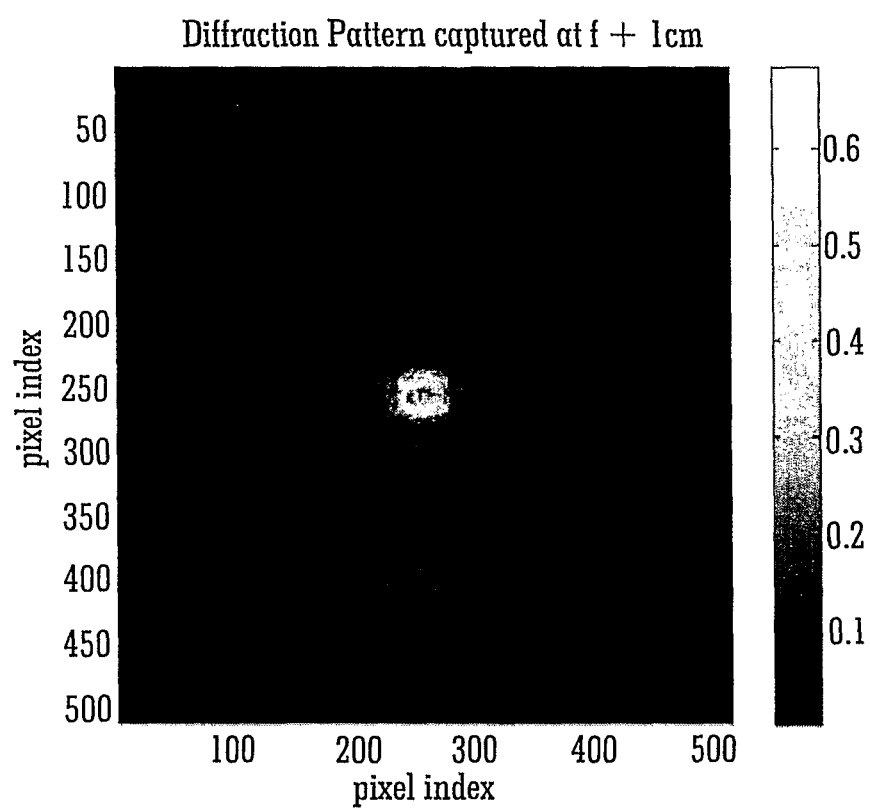
Figure 7:
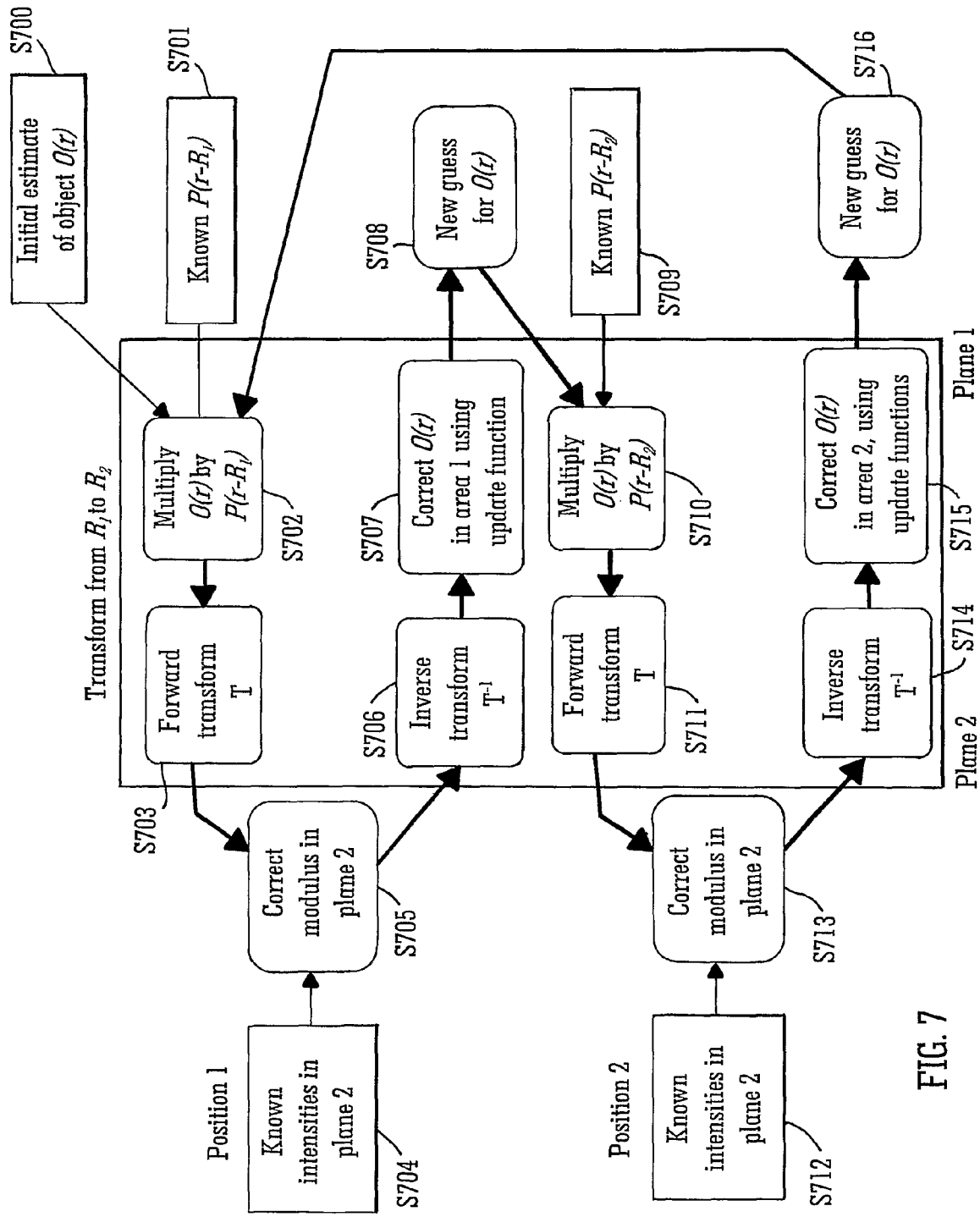
Figure 8:
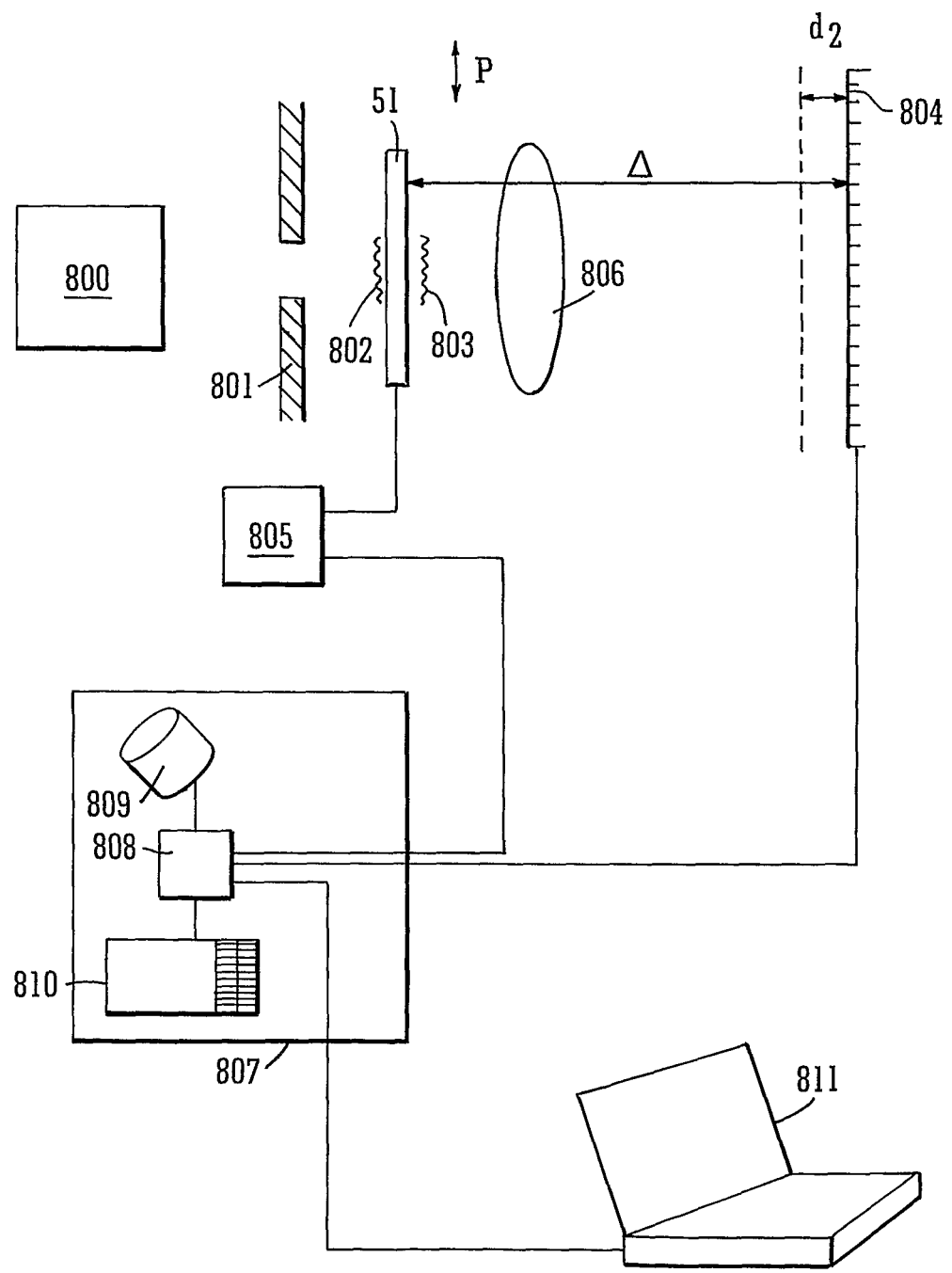

Embodiments of the present invention will now be described hereinafter, by way of example only, with reference to the accompanying drawings in which:

FIG. 1 illustrates diffraction;
FIG. 2 illustrates an arrangement used to generate a diffraction pattern with a target object;
FIG. 3 illustrates a diffraction pattern having a high dynamic range;
FIG. 4 illustrates a target object, downstream lens and diffraction pattern detection in an offset observation plane;
FIG. 5 illustrates a captured diffraction pattern with a detector at position A in FIG. 4;
FIG. 6 illustrates a captured diffraction pattern with a detector at position B in FIG. 4;
FIG. 7 illustrates an iterative phase retrieval scheme; and
FIG. 8 illustrates apparatus for providing image data.

In the drawings like reference numerals refer to like parts.

FIG. 4 illustrates how a scattering pattern may be developed and used to determine high resolution information about the structure of a target object. It will be understood that the term "target object" refers to any specimen or item placed in the path of incident radiation which causes scattering of that radiation. It will be understood that the target object should be at least partially transparent to incident radiation. The target object may or may not have some repetitive structure.

Incident radiation 40 is caused to fall upon the target object 41. It is to be understood that the term "radiation" is to be broadly construed and refers to energy from a radiation source. This will include, but is not limited to, electromagnetic radiation including X-rays, emitted particles such as electrons and/or acoustic waves. Such radiation may be represented by a wave function $\Psi(r)$. This wave function includes a real part and an imaginary part as will be understood by those skilled in the art. This may be represented by the wave functions modulus and phase. $\Psi(r)^*$ is the complex conjugate of $\Psi(r)$ and $\Psi(r)\Psi(r)^*=|\Psi(r)|^2$ where $|\Psi(r)|^2$ is an intensity which may be measured for the wave function.

The incident radiation 40 is scattered as it passes through and beyond the specimen 41. As such the wave function of the incident radiation as it exits the specimen will be modified in both amplitude and phase with respect to the wave function of the incident radiation at the pre-target side of the specimen. The scattering which occurs may include Fourier diffraction, refraction and/or Fresnel diffraction and any other form of scattering in which characteristics of the incident radiation are modified as a result of propagating after the specimen.

The target scatters the radiation into scattered wave components 42. It is to be noted that in FIG. 4 the width of the arrows' tails are selected to help illustrate the proportionality of the intensity of the waves whilst the arrow points show a direction of travel of the wave. A wave front 40 may arise from the collimation of a highly coherent source such as a laser. It will be understood that uncollimated radiation sources could be used in which instance several arrows would be needed to represent the waves emitted by the source. When the incident waves reach the diffracting target object scattering occurs with different waves travelling onward at a broad spread of angles. If the scattering effect caused by target object is small there will still be a large wave component (illustrated by an arrow having a large width) travelling straight through the structure with a zero or close to zero scattering angle. In comparison the scattered wave off axis will be significantly less intense. This is illustrated by an arrow having a relatively smaller width.

A lens 43 is located downstream of the target object. The scattered wave front hits the lens which focuses each wave component to a point in a plane 44. Each wave component is focused on a respective point on the observation plane with the location of a respective point being determined by the scattering angle of the particular wave component. The observation plane 44 identified by reference A in FIG. 4 corresponds to a back focal plane associated with the specific lens 43 utilised. If an array of detectors such as a CCD detector array is arranged in this plane a diffraction pattern will be detected. A Fourier diffraction pattern will form if the detectors are located a distance D from the specimen where D is sufficiently long for the diffraction pattern to be formed effectively from a point source.

FIG. 5 illustrates a diffraction pattern detected with a detector array arranged in the back focal plane A as shown in FIG. 4. The dynamic range of such a captured diffraction pattern is 123 db. By contrast in accordance with embodiments of the present invention the scattered radiation is detected in a plane offset from the back focal plane A. This new observation plane is illustrated as plane B in FIG. 4. The data with a low scattering angle including the wave component that passes unaffected through the target object is now spread across a region in the centre of the recorded diffraction pattern rather than being focused to a point. The effect is akin to blurring of vision in a person suffering from short-sightedness. The higher scattering angle data also spreads out but positive and negative interference ensures that these components retain an approximately constant intensity. The effect of moving the detector on a single diffraction pattern is illustrated in FIG. 6. Here the central bright area of FIG. 5 has spread to cover a larger area of the recorded pattern with a corresponding reduction in the maximum intensity present in the recording. As a result the dynamic range required to accurately capture the diffraction pattern is reduced by 14 db. The dynamic range of the diffraction pattern illustrated in FIG. 6 is 109 db.

As has previously been mentioned, the propagation of the waves arising from the diffracting structure when it is illuminated by a coherent plane wave can be modelled using a Fourier Transform, provided the plane of observation is in the back focal plane of a lens. For a diffraction pattern recorded beyond (or in front of) this plane to be useful in many applications, a model incorporating the extra propagation distance must be derived. To do this the Fourier Transform of a two-dimensional function f($\underline{r}$) is denoted as $\mathfrak{I}_f(\underline{v})$, where $\underline{r}$ and $\underline{v}$ are vectors describing the coordinates in their respective planes. If $\psi(\underline{r})$ is the complex-valued, two-dimensional function representing the transmissive properties of the diffracting structure, the diffraction pattern D($\underline{v}$) that results at the focal plane of the lens in FIG. 4 call it D($\underline{v}$), is given by:

$$D(\underline{v}) = \exp\left(j\frac{\pi}{f}(1 - d_1/f)|\underline{v}|^2\right)\mathfrak{I}_\psi(\underline{v}) \quad (1)$$

This is the conventional diffraction pattern, whose modulus is seen to be exactly the Fourier Transform of the diffracting structure, $\psi(\underline{r})$. To incorporate the extra propagation over the distance $d_2$ into the formula and arrive at the diffraction pattern $\Psi(\underline{k})$ in the observation plane (where $\underline{k}$ is an xy vector in the observation plane), a convolution is needed:

$$\Psi(\underline{k}) = Q(\underline{k}) \otimes D(\underline{v}) \quad (2)$$

$$Q(\underline{k}) = \exp\left(j\frac{\pi}{\lambda d_2}|k|^2\right)$$

Here, multiplicative constants have been ignored in the formulation. Q($\underline{k}$) may take a different form when the distance $d_2$ becomes very small. It will be understood that an entirely equivalent procedure would be to move the observation plane nearer to the lens, so that it lies between the lens and its back focal plane. In this case, $d_2$ is negative and so a change of sign in the exponent of Q($\underline{k}$) is the only adjustment necessary to model this new geometry.

To propagate wavefronts back from the observation plane to the diffracting structure, the steps detailed in equations 1 and 2 are reversed.

$$D(\underline{v}) = (Q'(\underline{v}) \otimes \Psi(\underline{k}))\exp\left(-j\frac{\pi}{f}(1 - d_1/f)|\underline{v}|^2\right) \quad (3)$$

$$Q'(\underline{v}) = \exp\left(-j\frac{\pi}{\lambda d_2}|\underline{v}|^2\right)$$

$$\psi(r) = \mathfrak{I}_D^{-1}(r) \quad (4)$$

Where $\mathfrak{I}^{-1}_f(\underline{r})$ is the inverse Fourier Transform of the function f.

Equations 1 to 4 allow the propagation of a wavefront between the diffracting structure and the plane of observation in FIG. 4 to be modelled. The improved recording enabled in this configuration can then be utilised in applications whose purpose is to provide information about the diffracting structure and where the accuracy of the recorded pattern is crucial to the generation of successful results.

In particular, but not exclusively, embodiments of the present invention can be utilised in a broad range of imaging applications. In one embodiment use is incorporated into an iterative phase retrieval scheme as described in WO 2005/106531 (which is incorporated herein by way of reference). Here, the recorded intensity of a diffraction pattern is combined with some a priori knowledge of the diffracting structure to provide a set of conditions that both the unknown phase of the diffraction pattern and the remaining unknown aspects of the diffracting structure must meet. These conditions are used in an iterative scheme to drive an initial random guess at the diffracting object toward a good estimate of its transmission function. A block diagram illustrates the general scheme in FIG. 7.

FIG. 7 illustrates a methodology for obtaining a wave function of an object and thus for obtaining image data which may be used subsequently to generate high resolution images of an object. FIG. 7 illustrates one possible method using an embodiment of the present invention illustrated in FIG. 8 and moving the aperture from a first position after measuring the diffraction pattern to a second position where a second respective diffraction pattern may be measured. It will be understood that embodiments of the present invention may use one or more positions for the aperture. Also embodiments can be used whereby rather than moving the aperture the location where the weakly focused radiation falls on the specimen may be selected. In this instance the lens may optionally be located upstream of the target object.

O(r) and P(r) represent two-dimensional complex functions, that is, each point in O(r) or P(r), where r is a two-dimensional coordinate, has associated with it a complex number. In what follows, O(r) will physically represent an exit wave that would emanate from an object function which is illuminated by a plane wave. For example, in the case of electron scattering, O(r) would represent the phase and amplitude alteration into an incident wave as a result of passing through the object of interest.

In what follows P(r) represents either an illumination function, such as that generated by a caustic or illumination profile formed by a lens or other optical component or a filtering function, such as an aperture or transmission grating mounted downstream of the object function.

It may be assumed in what follows that O(r) or P(r) can be moved relative to one another by various distances R. The nomenclature adopted is written in terms of moving P(r), although equivalently we could instead move O(r) relative to P(r). In both situations, the complex value of O(r) is altered by forming the product of O(r) with P(r–R) to give a total exit wave function of $\psi$(r), i.e.

$$\psi(r,R)=O(r)P(r-R) \quad 5$$

This will generally be satisfied. It is notable that there are very few practical restrictions on either the object function or the probe/aperture function. Neither function may be a plane wave, or periodic with a repeat distance that is a multiple of the difference between different values for R. This is because the algorithm requires several measurements that are different in order to work. In experimental practice these criteria are easy to satisfy.

The algorithm works to find the phase and intensity of the complex function ψ(r,R). It requires as input knowledge of the function P(r−R), and one or more (preferably several) measurements of the intensity of the wave function in a plane which is different to that containing the specimen. It is convenient to use the diffraction plane, which is related to the specimen plane by the Fourier transform. In this case the measured input data is the intensities of the diffraction patterns at one or more probe/aperture positions. Using diffraction data has several advantages, including ease of collection, no requirements for focussing the exit wave function into an image, and the increase of resolution achieved by measuring data at high angles.

However it is also possible to run the algorithm based on a set of defocused images measured at some distance from the exit surface of the specimen/aperture. In this situation the free space propagator is substituted for the Fourier transform.

The algorithm is not restricted to use of these two transforms. Other effective transforms could be used to move from one plane of information to the other. In what follows a general transform T is referred to that transforms a wave function from the first plane, called plane 1, to the second plane, called plane 2.

The algorithm works as follows and with reference to FIG. 7:

1. Start at step S700 with a guess at the object function $O_{g,n}(r)$, where the subscript g,n represents a guessed wave at the nth iteration of the algorithm. These functions are in plane 1 (which is the real space plane if the Fourier transform is used). Preferably the first guess of $O_{g,n}(r)$ equals unity at all points r. This corresponds to an absent specimen.

2. A known aperture in terms of position and characteristics is selected at step S701. This provides a probe function P(r−R). At step S702 the current guess at the object function is multiplied by the aperture or probe at the current position R, P(r−R). This produces the guessed exit wave function (still in plane 1) for position R, $$\psi_{g,n}(r,R)=O_{g,n}(r)P(r-R) \qquad 6$$

3. Next at step S703 a transformation of $\psi_{g,n}(r,R)$ to obtain the corresponding wave function in plane 2 (which would be the diffraction space plane if the Fourier transform is used), for that position R. Here T is used to represent some general transform that would often be the Fourier transform, but could also be the Fresnel free space propagator, or some other transform suited to a particular application of the algorithm.

$$\Psi_{g,n}(k,R)=T[\psi_{g,n}(r,R)] \qquad 7$$

k is the coordinate in plane 2. (For the Fourier transform, k would be the usual reciprocal space coordinate. For the propagator, k would be the xy coordinate in the defocused plane.) It is important to note that $\Psi_{g,n}(k,R)$ is a "guessed" version of the actual wave function in plane 2, since it has been produced by the guessed object function $O_{g,n}(r)$. Successive iterations of the algorithm will produce increasingly accurate versions of $\Psi_{g,n}(k,R)$.

Note that $\Psi_{g,n}(k,R)$ can be written in the form:

$$\Psi_{g,n}(k,R)=|\Psi_{g,n}(k,R)|e^{i\theta_{g,n}(k,R)} \qquad 8$$

where $|\Psi_{g,n}(k,R)|$ is the (guessed) wave function amplitude and $\theta_{g,n}(k,R)$ is the (guessed) phase in plane 2 at iteration n, for position R.

Here the transform needs to be modified as above described with respect to equations 1 and 2 to account for the fact that the observation plane is offset from the back focal plane of the lens.

By measuring the intensity of the diffraction pattern using the detector array information about the actual transformed exit wave function are known. A measured intensity of the diffraction pattern where the aperture is in a first position thus forms the basis of an estimate of the complex wave function of the diffraction pattern. However the measured intensity does not provide information about the phase of the wave function. Rather the measured intensity is comparable to the squared modulus of Ψ(r). That is $|\Psi(r)|^2$. Once the intensity of radiation in the diffraction pattern in plane 2 is known at step S704 then the following step may be carried out.

4. Correct, at step S705 the intensities of the guessed plane 2 wave function to the known values.

$$\Psi_{c,n}(k,R)=|\Psi(k,R)|e^{i\theta_{g,n}(k,R)} \qquad 9$$

where $|\Psi(k,R)|$ is the known plane 2 modulus. That is the square root of the measured intensity at the image plane.

5. Inverse transform S706 back to real space to obtain a new and improved guess at the exit wave function (in plane 1) ($T^{-1}$ represents the inverse of the previously used transform T), $$\psi_{c,n}(r,R)=T^{-1}[\Psi_{c,n}(k,R)] \qquad 10$$

Here the Fourier transform needs modifying in accordance with equations 3 and 4 to account for the fact that measurements are taken at an offset observation plane.

6. Update via step S707 the guessed object wave function in the area covered by the aperture or probe, using the update function $$O_{g,n+1}(r) = O_{g,n}(r) + \frac{|P(r-R)|^l P^*(r-R)}{|P_{max}(r-R)|^l (|P(r-R)|^2 + \delta)} \beta(\psi_{c,n}(r,R) - \psi_{g,n}(r,R)) \qquad (11)$$

where the parameters β, δ and l are appropriately chosen, and $|P_{max}(r-R)|$ is the maximum value of the amplitude of P(r). The result is a new guess for the object function (S708).

The update function helps make the effective deconvolution that occurs possible and introduces a weighting factor which causes the object function to be updated most strongly where the probe function has largest amplitude. The selectable constant l may be set to 1. It may be selected as any value in the range of 0 to 3 and need not be an integer value. It is useful to set l>1 when there is much noise. l may be selected l<1 when because of scattering geometry, the detected intensity is of the form of a Gabor hologram or similar. The value δ is used to prevent a divide-by-zero occurring if |P(r−R)|=0. δ is a small real number as is commonly applied in Weiner Filters and is usually (though not necessarily) smaller than $P_{max}$ and can be considerably smaller if the noise present in the recorded data is small. The constant β controls the amount of feedback in the algorithm, and may advantageously be varied between roughly 0.1 and 1. When β=less than 0.5, the previous estimate of the object is considered to be more important than the new estimate. Values in between vary the relative importance of the two estimates. β determines how quickly a solution is reached.

δ is a parameter which may be set at a fixed value or which may vary. It indicates how noisy the recorded data is and is used to attenuate how the updating is carried out in response to these circumstances. If good conditions exist for data collection that is to say with high beam current (high flux), which would imply low shot-noise, then it is safer to use results gathered to update the guessed estimate. Consequently the value of δ can be a small fraction of $P_{max}$ (e.g. less than $\frac{1}{10}^{th}$).

The expression:

$$\frac{|P(r-R)|^\ell}{|P_{max}(r-R)|^\ell} \qquad 12$$

maximises the update effect of regions where |P(r–R)| is large. This is useful, since it is those regions which are receiving the highest amount of incident radiation, and therefore which contain information with a relatively high signal to noise ratio. This information is clearly more valuable than that from regions where very little radiation is incident, and which is heavily affected by noise.

For the situation where β=1, l=0 and δ=0, and the function P(r–R) is a mask that is can be represented by a region where its value is unity while it is zero elsewhere, or support function, the algorithm has some similarities to the well known Fienup algorithm. If in this situation, only one position R is used, then the algorithm reduces to being mathematically identical to the basic Fienup algorithm. Where more than one position R is used, the algorithm has considerable advantages over known methods, including the fact that it does not suffer from uniqueness issues, and that a wider field of view may be imaged.

Subsequent to updating the running estimate of the guess the algorithm shown in FIG. 7 progresses to selecting a new position R which at least in part overlaps the previous position. The overlap should preferably be more than 20% and is preferably 50% or more. This may be achieved by either moving the aperture in the direction of arrow P shown in FIG. 8 by a predetermined amount or by causing the illuminating radiation to fall upon a different region of the target. It will be understood that embodiments of the present invention may successfully provide image data for one location of a target object without any change in location of an aperture or incident radiation being made. In such embodiments after step S708 the algorithm returns to step S702. Instead of the initial estimate of the object function O(r) being loaded in the new guess for O(r) of step S708 is loaded in. On each iteration the new guess for the object function will approximate closer and closer to the actual object function as on each iteration information of the known intensity and thus the known amplitude component of the incident radiation is added to improve the accuracy of the estimate.

Nevertheless the more preferable method is to move to a new position R which in part overlaps the previous position as shown in FIG. 7.

A known probe function $P(r-R_2)$ at the second position is identified at step S709 and then the step as above mentioned are repeated so that the new guess generated in step S708 is multiplied with the new known probe function identified at step S709. This is illustrated in step S710. Effectively this generates an exit wave function either post specimen or post aperture depending upon the embodiment concerned. The resulting exit wave function is propagated at step S711 to provide an estimate of the scattering pattern which should be detected at that position. The diffraction pattern is measured at step S712 which provides intensity information and thus amplitude information about the transformed wave function. The intensity information is used to correct the amplitude of the transformed wave function whilst phase information is retained at step S713. This corrected wave function is inversely propagated via Fourier transformation (when the image is formed in the far field), Fresnel transformation when the image is formed at a location where Fresnel diffraction dominates or by any other suitable transformation. This is illustrated at step S714. The running estimate of O(r) is then corrected according to the update function shown above at step S715 and the result is a new guess for the object function illustrated in step S716.

At this stage further movement of the illumination or aperture may be made to a third or further position. Again a location where some overlap occurs between previous illuminated locations is preferable. In this way the whole target object may optionally be mapped. Alternatively the new guess generated at step S716 may be repeated without further positioning knowing known diffraction pattern results. In FIG. 7 the iterative method is illustrated as being repeated by returning to step S702 in which the new guess generated at step S716 is input to the multiplication stage rather than the initial estimate of the object function supplied at step S700.

The iterative method may be repeated until a predetermined event occurs. For example the iteration may be repeated a predetermined number of times, for example 1000 times or until the sum squared error (SSE) is sufficiently small. The SSE is measured in plane 2, as $$SSE = \frac{(|\psi_{g,n}(k,R)|^2 - |\psi(k,R)|^2)^2}{N} \qquad 13$$

where N is the number of pixels in the array representing the wave function.

During the iteration process the most up-to-date guess of the object function provides a running estimate for that object function. When the iteration process is completed as determined by the occurrence of a predetermined event, the running estimate of the object function provides image data at the locations which are either illuminated by the incident radiation or which are selected by location of a post target object aperture. This image data includes amplitude and phase information which can subsequently be used to generate a high resolution image of the selected region of the target object.

FIG. 8 illustrates apparatus for providing image data which may optionally be used to construct an image of a region of a target object according to the above-described embodiment illustrated in FIGS. 4 and 7. It will be understood that the region imaged could be the whole or a part or parts of the whole of the target object. Also whilst the apparatus shown in FIG. 8 illustrates a transmission mode embodiments of the present invention may be used with a wholly or partly reflective target object with a suitable realignment of the optical arrangement. A source of radiation 800 provides illumination onto an aperture 801 which selects a portion of the radiation to illuminate a corresponding region of a target 51. The incident radiation is associated with an incident wave function 802 and an exit wave function 803. This exit wave function is propagated across distance D where a diffraction pattern is formed on an array of detectors 804. The distance D is advantageously sufficiently long so that the propagated exit wave function 803 forms a Fourier diffraction pattern in the far-field. The detector array provides at least one detector which can detect the intensity of radiation scattered by the target object 51. A locating device 805 is provided which may be a micro actuator and this can locate the target object at one or more locations as desired with respect to the detector array and/or the aperture 801. In this way radiation from source 800 may be made incident on different locations of the upstream surface of the target 51.

A lens 806 is used to at least weakly focus the radiation onto the detector array. The lens used is associated with a respective back focal plane which is separated from a plane of the detectors in the detector array by an offset distance $d_2$. It will be appreciated that the any suitable focusing element can be used according to the radiation type used. Also that the focusing element can be a single or multipart piece.

A control unit 807 provides control signals to the micro actuator and also receives intensity measurement results from each of the pixel detectors in the detector array 804. The control unit 807 includes a microprocessor 808 and a data store 809 together with a user interface 810 which may include a user display and a user input key pad.

The control unit may be connected to a further processing device such as a laptop 811 or PC for remote control. Alternatively it will be understood that the control unit 807 could be provided by a laptop or PC. The control unit 807 can automatically control the production of image data in real time. Alternatively or additionally a user can use the user interface 810 to select areas of the target object for imaging or provide further user input.

In use the source of radiation 800 illuminates the aperture 801 with radiation. The target object 51 is selectively located by the actuator 805 under control of the control unit 807. The radiation forms a diffraction pattern detected at respective locations by each of the detectors in the detector array 804. Results from these detectors is input to the control unit and may be stored in the data store 809. If only one position is being used to derive image data the microprocessor uses this detected information together with program instructions including information about the algorithm above-noted to derive the image data. However if one or more further positions are required prior to finalising the image data the control unit next issues signals to the actuator 805 which locates the specimen at another selected location. The actuator 805 may place the specimen at one of many different positions. After relocation a further diffraction pattern formed on the detector array is measured and the results stored in the control unit. As an example the array 804 may be a CCD array of 1200×1200 pixels. If no further intensity measurements are required image data may at this stage be generated by the control unit in accordance with the two newly stored sets of results using the algorithm above-noted. The raw image data may be displayed or utilised for some purpose or a high-resolution image generated from the image data may be displayed on the user interface 810 or remote display on a PC or other such device.

Embodiments of the present invention thus provide an iterative method for deriving data relating to a target object. The iterative method is applicable in an intelligent way so as to be able to cope with generalised illumination systems. In these the transmittance function of an aperture is weakly defined or a beam of radiation may be weakly focused. The lens and aperture or lens or aperture form a localised illumination function. In alternative embodiments rather than deriving information of an object, if the object is well known, information regarding the radiation or aperture itself may be derived.

Whilst embodiments of the present invention have been described in respect of the generation of images of a target object using gathered data, it will be appreciated that embodiments of the present invention are applicable to the generation of data per se and that a physical image for a user to look at need not always be generated. One particular use where the generation and manipulation of raw data itself can be used without generation of images is in the technical field of process control. Other examples where an image is not necessarily formed are of course applicable. For process control there is generally a requirement for products produced during a process to be manufactured within certain tolerances. That is to say the dimensions of a product or indeed some other characteristics such as transparency or colour must fall within a predetermined range of values. Embodiments of the present invention can be utilised either in transmittance mode or in reflective mode to establish a value associated with respective characteristics of a product and determine whether these characteristics such as length, width, height, shape, and/or transparency or the like satisfy manufacturing tolerances. It will be appreciated that the verification can be carried out in real time without an image of the product being analysed ever being produced. A simple visible and/or audible cue is merely sounded when a product has a characteristic which does not fall within predetermined satisfaction ranges.

It will be appreciated that embodiments of the present invention can be utilised to provide data relating to a 2D or 3D target object. A methodology for 3D imaging is disclosed in GB0709796.7 [Attorney Ref P116092 GB] which is hereby incorporated, by way of reference, in its entirety.

Embodiments of the present invention provide a method for obtaining image data suitable for subsequently generating a high resolution image of a part of a specimen at wave length-limited resolution. In this way a method and apparatus is provided which can produce image data having a far higher resolution than the resolution required for positioning accuracy of apparatus used to derive that information. In the case of very short wavelength radiation (sub-atomic) the resolution improvement may be 40 or more relative to prior art techniques. In some instances the resolution will be compromised by the atomic motions themselves.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. A method of providing image data for generating an image of a region of a target object, comprising:
   determining a back focal plane associated with at least one focusing element;
   locating at least one detector at a selected observation plane offset from the back focal plane associated with the at least one focusing element, the locating of the at least one detector occurring after the back focal plane is determined;
   providing incident radiation from a radiation source;
   focusing radiation via the at least one focusing element located downstream or upstream of the target object; and
   detecting an intensity of radiation scattered by the target object, via the at least one detector located downstream of the at least one focusing element at the selected observation plane offset from the back focal plane associated with the at least one focusing element.

2. The method as claimed in claim 1 further comprising:
   focusing radiation scattered by the target object with the at least one focusing element located downstream of the target object or focusing radiation from the radiation source with the at least one focusing element located upstream of the target object.

3. The method as claimed in claim 2, further comprising:
providing image data responsive to the detected intensity via an iterative process.

4. The method as claimed in claim 3 further:
detecting a first intensity of radiation scattered by said target object with the incident radiation at a first position with respect to the target object;
re-positioning the incident radiation relative to the target object; and
subsequently detecting a second intensity of radiation scattered by said target object with the incident radiation at a second position;
wherein said image data is provided responsive to the detected first intensity at said first position and the second detected intensity at said second position.

5. The method as claimed in claim 3 wherein said providing said image data comprises:
estimating an object function indicating at least one characteristic of said region of the target object; and
iteratively re-estimating said object function, whereby accuracy of a running estimate of the object function is improved with each iteration.

6. The method as claimed in claim 5 further comprising:
multiplying the estimated object function by a probe function indicating at least one characteristic of the incident radiation at said target object;
providing an exit wave function responsive to a result of said multiplication;
propagating the exit wave function to provide an estimate of an expected scattering pattern; and
correcting at least one characteristic of said expected scattering pattern according to a detected intensity.

7. The method as claimed in claim 6 further comprising:
inverse propagating the corrected expected scattering pattern having the corrected at least one characteristic to provide an updated exit wave function; and
updating the running estimate of the object function responsive to said updated exit wave function according to the update function:

$$O_{gn+1}(r)=O_{gn}(r)+U(r(\Psi_{cn}(r,R)-\Psi_{gn}(r,R))),$$

where $O_{gn+1}(r)$ is an updated object function, $O_{gn}(r)$ is an object function, $U(r)$ is an update function, $\Psi_{gn}(r,R)$ is a guessed plane 2 wave function, and $\Psi_{cn}(r,R)$ is a corrected plane 2 wave function.

8. The method as claimed in claim 7 wherein said update function is:

$$U(r) = \frac{\beta|P(r-R)|^\ell P*(r-R)}{|P_{max}(r-R)|^\ell (|P(r-R)|^2 + \delta)}$$

where $U(r)$ is the update function, $\beta$ is a value which controls an amount of feedback, $P(r)$ is an illumination or filtering function, R is a movement distance between $O(r)$ and $P(r)$, $P_{max}(r-R)$ is a maximum value of the amplitude of $P(r-R)$, $l$ is a constant and $\delta$ is a real number.

9. The method as claimed in claim 6 wherein said propagating comprises:
propagating the exit wave function using a modified Fourier transformation.

10. The method as claimed in claim 9, further comprising:
providing a modified Fourier transform given by:

$$\Psi(k)=Q(k)\otimes D(v)$$

where $D(v)$ is a definition of an expected defraction pattern in the back focal plane and $Q(k)$ is a modifying factor responsive to the offset of the observation plane from the back focal plane.

11. The method as claimed in claim 10, further comprising:
providing the convolution of the expected defraction pattern with a modification factor $Q(k)$ given by:

$$Q(k) = \exp\left(j\frac{\pi}{\lambda d_2}|k|^2\right)$$

where $d_2$ is the offset of the observation plane from the back focal plane.

12. The method as claimed in claim 6 wherein said corrected expected scattering pattern is corrected according to:

$$\Psi_{cn}(k,R)=|\Psi(k,R)|e^{i\Theta gn(k,R)}$$

where $\Psi_{cn}(k,R)$ is a corrected wave function, $|\Psi(k,R)|$ is the known plane 2 amplitude and $\Theta g n(k,R)$ the guessed plane 2 phase.

13. The method as claimed in claim 6 wherein propagation is:

$$\Psi_{gn}(k,R)=T[\Psi_{gn}(r,R)]$$

where $\Psi_{gn}(k,R)$ is a guessed wave function in plane 2, $T^{-1}$ indicates a transformation and $\Psi_{gn}(r,R)$ is a guessed plane 1 wave function.

14. The method as claimed in claim 6 wherein said inverse propagation is calculated according to:

$$\Psi_{c,n}(k,R)=T-1[\Psi_{c,n}(k,R)]$$

where $\Psi_{c,n}(k,R)$ is a guessed wave function in plane 1, $T^{-1}$ illustrates an inverse transformation procedure and $\Psi_{c,n}(k,R)$ is a corrected wave function in plane 2.

15. The method as claimed in claim 3 further comprising:
detecting a first intensity of radiation scattered by said target object with a post-target object aperture located at a first position with respect to the target object;
re-positioning the aperture relative to the target object; and
subsequently detecting a second intensity of radiation scattered by said target object with the aperture at a second position;
wherein said image data is provided responsive to the detected first intensity at said first position and the detected second intensity at said second position.

16. The method as claimed in claim 3 wherein said providing said image data comprises:
estimating an object function indicating at least one characteristic of a post-target object wave function immediately before a post-target object aperture; and
iteratively re-estimating said object function; whereby accuracy of a running estimate of the object function is improved with each iteration.

17. The method as claimed in claim 16 further comprising:
multiplying the estimated object function by a probe function indicating at least one characteristic of the post-target object aperture;
providing an exit wave function responsive to a result of said multiplication;
propagating the exit wave function to provide an estimate of an expected scattering pattern; and correcting at least one characteristic of said expected scattering pattern according to the first detected intensity and the second detected intensity.

18. The method as claimed in claim 1 wherein said incident radiation comprises a substantially localized wave field.

19. The method as claimed in claim 1 further comprising:
providing said image data for the region of said target object in real time.

20. A non-transitory computer-readable medium storing computer program instructions that, when executed by a computer, cause the computer to:
determine a back focal plane associated with at least one focusing element;
locate at least one detector at a selected observation plane offset from the back focal plane associated with the at least one focusing element, the at least one detector located at the selected observation plane after the back focal plane is determined;
provide incident radiation from a radiation source;
focus radiation via the at least one focusing element located downstream or upstream of the target object; and
detect an intensity of radiation scattered by the target object, via the at least one detector located downstream of the at least one focusing element at the selected observation plane offset from the back focal plane associated with the at least one focusing element.

21. A non-transitory computer-readable medium storing computer program instructions that, when executed by a computer, cause the computer to:
determine a back focal plane associated with at least one focusing element;
locate at least one detector at a selected observation plane offset from the back focal plane associated with the at least one focusing element, the at least one detector located at the selected observation plane after the back focal plane is determined;
provide incident radiation from a radiation source;
focus radiation via the at least one focusing element located downstream or upstream of the target object;
detect an intensity of radiation scattered by the target object, via the at least one detector located downstream of the at least one focusing element at the selected observation plane offset from the back focal plane associated with the at least one focusing element;
generate an image data based on intensity of radiation that is detected; and
display an image of a region of the target object on a user display based on the image data that is generated.

22. Apparatus for providing image data for generating an image of a region of a target object, comprising:
a radiation source that provides incident radiation;
at least one focusing element that focuses the radiation and is located downstream or upstream of a target object, the at least one focusing element having a predetermined back focal plane;
at least one detector located downstream of the at least one focusing element that detects an intensity of radiation scattered by the target object at a selected observation plane, the at least one detector being located at a selected observation plane that is offset from the predetermined back focal plane associated with the at least one focusing element, the location of the selected observation plane being based on the predetermined back focal plane; and
at least one processor that locates the at least one detector at the selected observation plane offset from the back focal plane associated with the at least one focusing element.

23. The apparatus as claimed in claim 22, further comprising:
at least one locating unit that locates the target object at a predetermined location and locates incident radiation or an aperture, located downstream of the target object, at one or more locations with respect to the target object.

24. The apparatus as claimed in claim 22, further comprising:
at least one processing unit that provides image data responsive to a detected intensity of scattered radiation.

25. The apparatus as claimed in claim 24 wherein said processing unit comprises:
a microprocessor;
a data store for holding data and instructions for said microprocessor; and
a processor for providing instructions to move one of said incident radiation or said aperture or a located target object.

26. The apparatus as claimed in claim 24 wherein said at least one processing unit further comprises:
a user interface comprising a user input device for enabling a user to input data, and a user display for displaying said image data or a high resolution image generated from said image data.

27. The apparatus as claimed in claim 22 wherein said radiation source comprises a source of coherent radiation.

28. The apparatus as claimed in claim 22 wherein said radiation source is an electron beam generator or an X-ray beam generator.

* * * * *